United States Patent
Saguchi et al.

[11] Patent Number: 6,132,749
[45] Date of Patent: Oct. 17, 2000

[54] SUSTAINED RELEASE PHEROMONE-CONTAINING PREPARATIONS

[75] Inventors: Ryuichi Saguchi; Hiroshi Suzuki, both of Niigata; Hachiro Saitoh, Kanagawa, all of Japan

[73] Assignee: Shin-Etsu Chemical Co., Ltd., Tokyo, Japan

[21] Appl. No.: 09/136,345

[22] Filed: Aug. 19, 1998

Related U.S. Application Data

[63] Continuation of application No. 08/574,241, Dec. 18, 1995, abandoned.

[30] Foreign Application Priority Data

Dec. 22, 1994 [JP] Japan ................................. 6-319909

[51] Int. Cl.$^7$ .................................................. A01N 25/08
[52] U.S. Cl. ........................ 424/409; 424/411; 424/486; 424/487; 424/501
[58] Field of Search ................................. 424/405, 409, 424/411, 486, 487, 501

[56] References Cited

U.S. PATENT DOCUMENTS 5,163,994  11/1992  Klimesch et al. ........................ 424/411
5,750,129   5/1998  Wakarchuk ............................... 424/408

FOREIGN PATENT DOCUMENTS

| 0 243 007 | 10/1987 | European Pat. Off. . |
| 0 305 139 | 3/1989  | European Pat. Off. . |
| 0 537 783 | 6/1995  | European Pat. Off. . |
| 37 08 297 | 9/1988  | Germany . |

OTHER PUBLICATIONS

Saito, translation of JP 6–192024, Jul. 12, 1994.
CAS abstract 121:198566, 1994, vol. 121, p. 449.

*Primary Examiner*—Jeffrey C. Mullis
*Attorney, Agent, or Firm*—Reed Smith Shaw & McClay LLP

[57] ABSTRACT

A sustained release pheromone-containing preparation is obtained by incorporating a sex pheromone having a heat of evaporation ranging from 21,000 to 27,000 cal/mole and a parameter, as a measure for the solubility, ranging from 8 to 9 $cal^{1/2}cm^{-2/3}$ into powder of a synthetic resin, whose parameter, as a measure for the solubility, ranges from 8 to 9.5 $cal^{1/2}cm^{-2/3}$, having an average particle size ranging from 0.2 to 2.5 mm. The sustained release pheromone-containing preparation can be sprayed using a widely used spraying machine and can release the sex pheromone at an almost constant concentration over a long period of time.

5 Claims, 1 Drawing Sheet

SUSTAINED RELEASE PHEROMONE-CONTAINING PREPARATIONS

This is a continuation of Ser. No. 08/574,241, filed Dec. 18, 1995, now abandoned.

BACKGROUND OF THE INVENTION

The present invention relates to a sustained release pheromone-containing preparation which is used to control the proliferation of harmful insects through disturbance of the copulative communication thereof.

Recently, pheromones have been attracted special interest as substances having an effect of controlling the proliferation of harmful insects. Among these, the sex pheromones have most widely been used as the pheromones capable of being easily used and having a strong effect of inhibiting proliferation of harmful insects. The sex pheromone is a signal substance which is released by an insect in order to attract the insect of the other sex upon copulation. The pheromones have not been able to be used for controlling harmful insects until pheromones having structures quite similar to those of the naturally occurring substances can be synthesized.

There has been known the communication-disturbing method as a means for controlling the breeding of harmful insects. The term "communication-disturbing method" herein used comprises distributing a sustained release pheromone-containing preparation in fields to thus lower the ability of male or female insects to recognize the individual opposite sex and to confirm the positions thereof and to thereby inhibit copulation of the insects.

The sustained release pheromone-containing preparation must satisfy the following requirements. That is, it can release a sex pheromone in a desired amount over a desired period of time; the amount of the released pheromone per unit time is uniform throughout the releasing time; and the whole pheromone contained therein can be released within a predetermined period of time. In addition, it is sometimes required for the pheromone-containing preparation to satisfy such a requirement that it should be formed into fine particles or a suspension in order to improve the operations for spraying and application.

Examples of such sustained release pheromone-containing preparations which can satisfy the foregoing requirements include those prepared by mixing a pheromone with an inorganic substance, adding a binder to the resulting mixture and then subjecting it to granulation as disclosed in Japanese Patent Provisional Publication No. 59-139301; those comprising a pheromone which is encapsulated into micro-capsules as disclosed in U.S. Pat. No. 2,800,457, U.S. Pat. No. 2,800,458 and U.S. Pat. No. 3,577,515; and those comprising a pheromone impregnated into a polymer resin as disclosed in U.S. Pat. No. 4,111,684, U.S. Pat. No. 3,639,306 and U.S. Pat. No. 4,962,170.

Among these, the pheromone-containing preparations which are prepared by mixing a pheromone with an inorganic substance and then formed into granules cannot uniformly release the pheromone contained therein. Moreover, they have a particular external shape and therefore, they require the use of a specific spraying machine for distributing them over a wide area. In case of the sustained release pheromone-containing preparations which comprise pheromones encapsulated into micro-capsules, it is impossible to control the release rate of a sex pheromone by reducing the release surface area per unit weight thereof since the micro-capsules having a diameter of not less than 0.2 mm cannot be prepared due to the technical limit in the production thereof. Moreover, the capsule covering the surface of the preparation also has low mechanical strength. For this reason, the sustained release pheromone-containing preparations which have widely been used comprise polymer resins impregnated with pheromones.

An example of the sustained release pheromone-containing preparations which comprise polymer resins impregnated with pheromones comprises a pheromone which is loaded on polymer powder. The preparation comprising a pheromone loaded on polymer powder has a large surface area per unit weight of the pheromone. Therefore, the amount of the released pheromone goes to excess in case of such a preparation and therefore, the preparation is effective over a very short period of time. Moreover, the pheromone-containing preparation undergoes the blocking phenomenon in which particles present on the surface of the preparation cause surface migration to thus adhere to one another due to, for instance, an increase in the storage temperature. As a means for preventing the blocking phenomenon, Japanese Patent Provisional Publication No. 64-208532 discloses a sustained release pheromone-containing preparation in which the pheromone is admixed with powder of a polymer resin carrying hydrophilic hydroxyl groups. Moreover, Japanese Patent Provisional Publication Nos. 56-148402 and 6-192024 each discloses a sustained release pheromone-containing preparation in which a powdery resin is adhered to the surface of the particles of the preparation. As has been discussed above, it is inevitable that the preparation must be subjected to a secondary processing in order to prevent the blocking phenomenon.

SUMMARY OF THE INVENTION

The present invention has been developed to solve the foregoing problems associated with the conventional techniques and accordingly, it is an object of the present invention to provide a sustained release pheromone-containing preparation which can be sprayed using spraying machines widely used and can release the pheromone included therein at an almost constant concentration over a long period of time.

The sustained release pheromone-containing preparation which has been developed to accomplish the foregoing object comprises a sex pheromone included in powder, having an average particle size ranging from 0.2 to 2.5 mm, of a synthetic resin which is compatible with the pheromone.

DETAILED DESCRIPTION OF THE INVENTION

Figure 1:
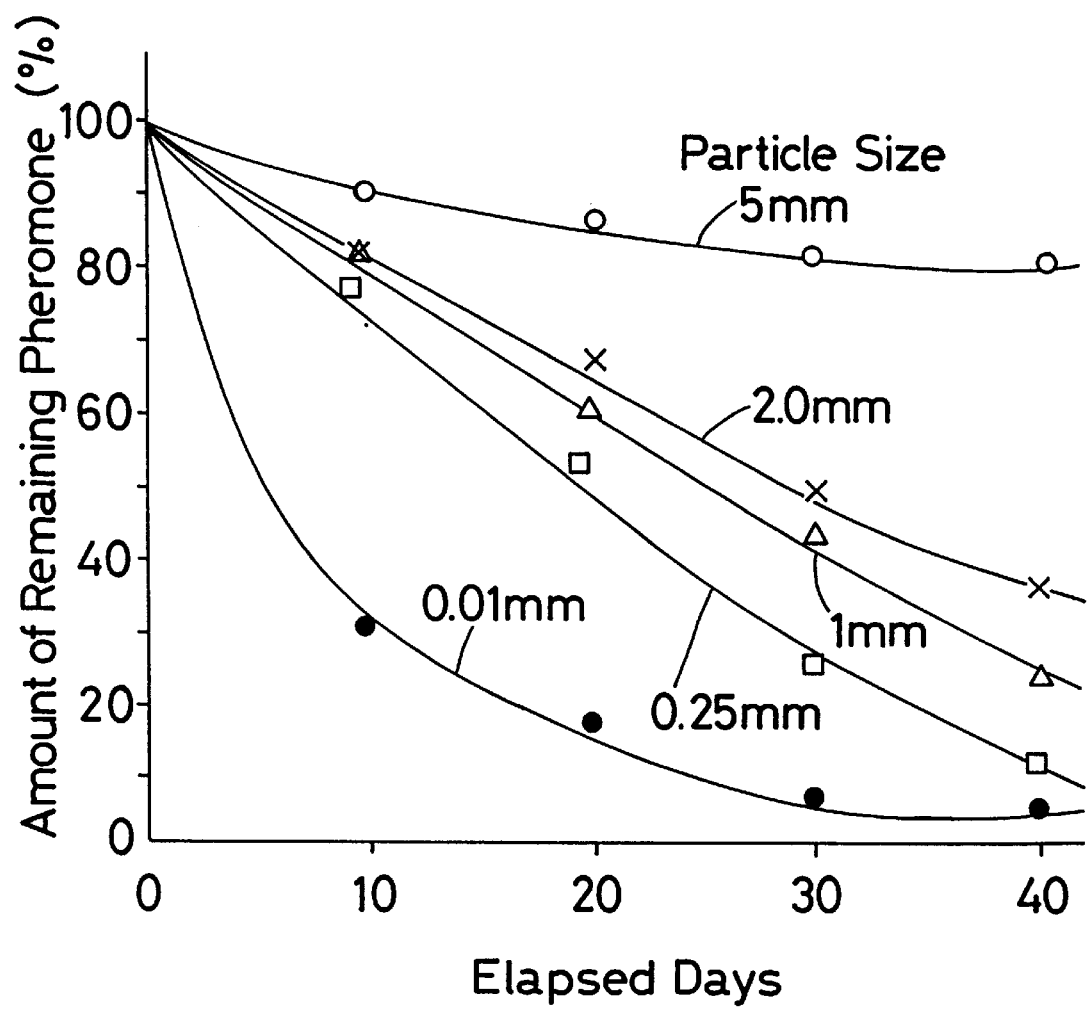
FIG. 1 attached hereto is a diagram showing the relation between the volatility rate of a sex pheromone and the average particle size of powder of an ethylene-vinyl acetate copolymer which comprises the sex pheromone.

The synthetic resin used in the sustained release pheromone-containing preparation of the present invention and compatible with the sex pheromone is preferably a powdery resin having an average particle size ranging from 0.2 to 2.5 mm. If the particle size of the synthetic resin is less than 0.2 mm, the surface area thereof per unit weight is too large, the initial volatility rate of the sex pheromone is in turn extremely high and almost all of the sex pheromone is released within a short period of time. Therefore, the resulting pheromone-containing preparation cannot control harmful insects over a long time period. On the other hand, if it exceeds 2.5 mm, the surface area thereof per unit weight is too small and the volatility rate of the sex pheromone in turn low. Moreover, it takes a long time for the pheromone is sex pheromone present in the deep part of the resin particles to arrive at the vacant portions on the surface remaining after volatilization of the sex pheromone present on the particle surface and accordingly, the volatilization of the sex pheromone is rapidly finished as a matter of fact, because of a large particle size of the powdery resin.

The content of the sex pheromone in the synthetic resin preferably falls within the range of from 0.3 µg to 3 mg/resin particle. The pheromone-containing preparation having a sex pheromone content falling within the range defined above permits, under the usual weather conditions, the control of harmful insects over a long period of time. If the content is less than 0.3 µg, the sex pheromone is not volatilized in an amount required for disturbing the copulation of harmful insects. On the other hand, any further effect of the sex pheromone cannot be expected any more even if the preparation includes the pheromone in a content more than 3 mg and the use of such a preparation is unfavorable from the economical standpoint.

The heat of evaporation of the sex pheromone preferably ranges from 21,000 to 27,000 cal/mole. If it is less than 21,000 cal/mole, the sex pheromone is excessively released from the sustained release preparation containing the same and accordingly, the preparation does not ensure the release of the pheromone over a long time period, while if it exceeds 27,000 cal/mole, the release of the sex pheromone is too small to sufficiently control harmful insects. In particular, if the synthetic resin has an average particle size defined above and the pheromone-containing preparation has a pheromone content falling within the range defined above, the heat of evaporation of the sex pheromone particularly preferably ranges from 21,800 to 27,000 cal/mole to ensure the release of the pheromone at a constant concentration over a long time period on the order of several tens of days.

The sex pheromone used herein preferably has a solubility parameter, as a measure for the solubility thereof, ranging from 8 to 9 $cal^{1/2}cm^{3/2}$. The term "compatibility of a pheromone with a synthetic resin (or vice versa)" herein used means such properties that one of these substances has an affinity for the other substance and they can form a solution or an intimate mixture. More specifically, one of two kinds of substances compatible with one another can include the other substance in a high concentration and does not rapidly release the latter, but gradually volatilize the same. The sustained release pheromone-containing preparation according to the present invention does not cause any condensation and sublimation of the pheromone and is free of any blocking, i.e., adhesion of particles, during storing the preparation, since the sex pheromone and the synthetic resin are compatible with one another. Accordingly, if the solubility parameter as a measure for the solubility of the pheromone is beyond the range of from 8 to 9 $cal^{1/2}cm^{3/2}$, the pheromone is insufficiently soluble in the synthetic resin, the amount of the pheromone capable of being incorporated into the polymer is limited and the resulting preparation does not exhibit any sustained release property at all.

The sex pheromones usable in the present invention preferably have a molecular weight ranging from 220 to 330, in particular, 250 to 310. The molecular weight thereof has an effect on the release rate of the pheromone and the concentration thereof released and the releasing time thereof varies depending on the molecular weight. If the molecular weight of the pheromone is less than 220, the vapor pressure of the sex pheromone released is too high and the release rate thereof is in turn too high to release the same over a long time period. On the other hand, if it exceeds 330, the vapor pressure of the sex pheromone released is too low to ensure the pheromone concentration in the air sufficient for disturbing the copulation of harmful insects.

Examples of sex pheromones usable herein include 14-methyl-1-octadecene, Z9-tricosene, E4-tridecenyl acetate, dodecyl acetate, Z7-dodecenyl acetate, Z8-dodecenyl acetate, Z9-dodecenyl acetate, E7,Z9-dodecadienyl acetate, Z9-tetradecenyl acetate, E11-tetradecenyl acetate, Z11-tetradecenyl acetate, Z9,E11-tetradecadienyl acetate, Z9,E12-tetradecadienyl acetate, Z11-hexadecenyl acetate, Z7,Z/E11-hexadecadienyl acetate, Z13-hexadecatrienyl acetate, Z13-octadecenyl acetate, E13, Z13-octadecadienyl acetate, Z11-hexadecenal, Z13-octadecenal, Z13-icosen-10-one, 7,8-epoxy-2-methyloctadecane and 8-methyl-2-decyl propionate. These sex pheromones may be used alone or in any combination. Moreover, they may, if necessary, be used in combination with other various additives such as antioxidants and/or ultraviolet light absorbers.

The solubility parameter of the synthetic resin which is compatible with the sex pheromone preferably ranges from 8 to 9.5 $cal^{1/2}cm^{-2/3}$. If the parameter is beyond the range defined above, i.e., the parameter of the synthetic resin deviates from that of the sex pheromone, the synthetic resin loses its compatibility with the sex pheromone. The synthetic resins usable herein are those showing compatibility with the sex pheromones, in particular, widely used resins excellent in processability and desirably used are olefinic copolymers carrying polar groups such as carboxyl groups. Such olefcinic copolymers may be, for instance, copolymers of ethylene and vinyl esters and copolymers of ethylene and α- or β-unsaturated carboxylic acids or derivatives thereof. Specific examples thereof include ethylene-vinyl acetate copolymer (8.0 to 9.6 $cal^{1/2}cm^{3/2}$), ethylene-acrylic acid ester copolymer (8.0 to 9.8 $cal^{1/2}cm^{3/2}$) and ethylene-methacrylic acid ester copolymer(8.0 to 9.2 $cal^{1/2}cm^{3/2}$). The acceptable range for the parameter of each copolymer is given in the parenthesis. If the compositions of these copolymers can variously be changed so that the parameter thereof falls within the range of from 8.0 to 9.5 $cal^{1/2}cm^{3/2}$ to thus make it close to that of the pheromone, the compatibility of the copolymers with the sex pheromones can highly be improved. Among these copolymers, ethylene-vinyl acetate copolymers are particularly preferred because of their cheapness and easy availability.

The ethylene copolymers carrying polar groups such as carboxyl groups may be used in combination with other olefinic polymers. Examples of such other polymers used in combination therewith include such as polyethylene, polypropylene and polybutylene; homopolymers and copolymers of these olefinic monomers and other copolymerizable monomers. The non-polar olefinic copolymers serve to increase the diffusion rate or the concentration of the evaporated sex pheromones and therefore, the volatility rate of the sex pheromone can be controlled by properly selecting the kinds and mixing ratio thereof. For instance, the higher the rate of the olefinic polymer, the higher the volatility rate of the pheromone.

The sustained release pheromone-containing preparation may be treated with a coating agent to cover individual particles thereof. If the volatility rate of the sex pheromone is too high, the rate can be controlled by covering the particles of the preparation with such a coating agent. The coating agent may be any substance inasmuch as it can make the permeation of the sex pheromone therethrough difficult and examples thereof are poly(methyl methacrylate), polyvinylidene chloride, polyvinyl alcohol, polystyrene, polyvinyl chloride, polyamide and polyethylene terephthalate. Alternatively, it is also possible to partially adhere inorganic powder which may inhibit the permeation of the sex pheromone therethrough or to partially adhere synthetic resin powder incompatible with the sex pheromone to individual particles of a synthetic resin.

The foregoing sustained release pheromone-containing preparation according to the present invention can be prepared by mixing and kneading a synthetic resin and a sex pheromone in an extruder, then forming the mixture into particles, optionally grinding the particles in a pulverizer and classifying into particles having a desired particle size. Alternatively, the pheromone-containing preparation can likewise be prepared by impregnating pellets of a synthetic resin with a sex pheromone and then finely pulverizing the pellets to a desired particle size, or by impregnating synthetic resin powder with a sex pheromone and then finely pulverizing the pellets to a desired particle size.

The powder of the preparation may be surface-coated by, for instance, spraying the powder of a synthetic resin impregnated with a sex pheromone with a coating agent such as poly(methyl methacrylate).

The resulting sustained release pheromone-containing preparation is uniformly distributed in fields. The method for distributing the preparation is by no means restricted to a specific one. More specifically, the preparation may be distributed as such or may be sprayed after adding the sustained release pheromone-containing preparation and a water-soluble adhesive such as an acrylic adhesive to water to give a suspension. The preparation is preferably sprayed immediately before the copulation period of harmful insects.

The sustained release pheromone-containing preparation of the present invention comprises a powdery substance having a particle size ranging from 0.2 to 2.5 mm which is impregnated with a sex pheromone, i.e., it does not have a particular shape and therefore, it can be sprayed using a widely used spraying machine.

Substances having parameters, each serving as a measure for the solubility thereof, which are very close to one another are excellent in compatibility with one another and therefore, one of the substance can contain the other substance in a high concentration. In the sustained release pheromone-containing preparation according to the present invention, the parameters of a sex pheromone and a synthetic resin as the ingredients of the preparation are very close to one another. Accordingly, the sex pheromone never undergoes condensation and/or sublimation and the preparation does not undergo adhesion between particles of the synthetic resin, i.e., is free of any blocking. One of substances which are compatible with one another serves to gradually evaporate and release the other substance included therein. Therefore, the sustained release pheromone-containing preparation can gradually release the sex pheromone at a constant and low rate over a long period of time under the usual weather conditions. Incidentally, the parameter is determined by the size of the molecule and the heat of evaporation thereof.

Examples of the present invention will hereinafter be explained in more detail.

EXAMPLE 1

Pellets (90 parts by weight) of an ethylene-vinyl acetate copolymer (trade name: Ultracene UE632 available from Tosoh Corporation; having a parameter (hereunder referred to as "$\delta$"), as the measure for the solubility, of $8.4\ cal^{1/2}cm^{3/2}$) were impregnated with 10 parts by weight of Z11-hexadecenyl acetate (heat of evaporation (hereunder referred to as "E")=24,075 cal/mole; $\delta=8.7\ cal^{1/2}cm^{3/2}$) as a component of the sex pheromone of diamondback moth (*Plutella xylostella* Linne) and then pulverizing the pellets in a pulverizer to give a sustained release pheromone-containing preparation having a particle size of 2.0 mm. The same procedures used above were repeated to give sustained release pheromone-containing preparations having particle size of 1.0 mm and 0.25 mm respectively.

The resulting sustained release pheromone-containing preparations having different particle sizes each was allowed to stand under the predetermined conditions, i.e., a temperature of 40° C. and a wind velocity of 0.3 m/sec to determine the amount of the sex pheromone remaining in each preparation. The results thus obtained are listed in the following Table 1. Moreover, the results listed in Table 1 are plotted on FIG. 1 in the form of a graph.

The resulting sustained release pheromone-containing preparations each was packed in a gas barrier film, stored at a temperature of 40° C. for 2 months and then unpacked to inspect the preparation for any blocking, but these preparations did not undergo any blocking at all.

COMPARATIVE EXAMPLE 1

The same procedures used in Example 1 were repeated to prepare two kinds of sustained release pheromone-containing preparations except that the average particle sizes of the resulting pheromone-containing preparations obtained after pulverization were controlled to 0.01 and 5.0 mm respectively. The results obtained are summarized in the following Table 1 and plotted on FIG. 1.

TABLE 1

|  | Particle Size(mm) | Rate (%) of Remaining Sex Pheromone | | | |
| --- | --- | --- | --- | --- | --- |
|  |  | After 10 Days | After 20 Days | After 30 Days | After 40 Days |
| Ex. 1 | 2.0 | 82 | 68 | 50 | 35 |
|  | 1.0 | 80 | 60 | 43 | 25 |
|  | 0.25 | 78 | 52 | 25 | 12 |
| Comp. Ex. 1 | 5.0 | 90 | 85 | 80 | 78 |
|  | 0.01 | 30 | 15 | 8 | 4 |

The foregoing results clearly indicate that the sustained release pheromone-containing preparations prepared in Example 1 each releases the sex pheromone at a constant rate over 40 days.

COMPARATIVE EXAMPLE 2

A sustained release pheromone-containing preparation having an average particle size of 0.8 mm was prepared by repeating the same procedures used in Example 1 except that 10-methyl-tridecan-2-one (E=18,965 cal/mole; $\delta=8.7\ cal^{1/2}cm^{3/2}$) was used as the pheromone to be loaded.

The resulting pheromone-containing preparation was allowed to stand in a room to determine the amount of the pheromone remaining in the preparation. As a result, it was found out that the diffusion rate of the pheromone in the preparation was very high and the release of the pheromone was correspondingly completed within only about two weeks.

COMPARATIVE EXAMPLE 3

A sustained release pheromone-containing preparation having an average particle size of 0.25 mm was prepared by repeating the same procedures used in Example 1 except that Periplanone B, represented by the formula (1R, 2R, 5E, 7S, 10R) −1Z, 5E-1,10(14)-Diepoxy-4(15),5-germacradien-9-one, (E=22,040 cal/mole; δ=10.0 cal$^{1/2}$cm$^{3/2}$) was used as the pheromone to be loaded.

The resulting sustained release pheromone-containing preparation was packed in a gas barrier film, stored at a temperature of 40° C. for 2 months and then unpacked to inspect the preparation for any blocking. As a result, it was found that the preparation caused blocking and partially caused agglomeration.

EXAMPLE 2

There were mixed and kneaded, in a kneader, 1 kg of Z7,Z/E11-hexadecadienyl acetate (E=23,775 cal/mole; δ=8.7 cal$^{1/2}$cm$^{3/2}$) and 9 kg of an ethylene-vinyl acetate copolymer, followed by extruding the mixture into rods and finely cutting into pellets. The specific gravity thereof was found to be 0.95. Then the resulting pellets were ground using a pulverizer to give a powdery sustained release pheromonecontaining preparation having an average particle size of 0.3 mm.

Then 2.4 kg of the powdery pheromone-containing preparation was mixed with 60 kg (solid content 50%) of an oil-in-water type (hereinafter referred to as "O/W type") emulsion of an acrylic adhesion and 60 l of water was added to the resulting mixture. The resulting suspension was sprayed on cotton plant in a field of 8 hectares in Parker District, Ariz., U.S.A. on August, 1992 using an aerial applicator.

At this stage, the pheromone traps for pink bollworm were simultaneously set up within the same cotton field in order to confirm the communication-disturbing effect of the pheromone-containing preparation and the number of male imagines attracted and killed by the traps was determined, which was regarded as copulation. As a result, there was not observed any male image attracted and killed within 6 weeks immediately after the spraying. This clearly indicates that the sustained release pheromone-containing preparation shows a high effect of disturbing the copulative communication.

EXAMPLE 3

There were mixed and kneaded, in a kneader, 0.5 kg of 7,8-epoxy-2-methyloctadecane (E=21,905 cal/mole; δ=8.2 cal$^{1/2}$cm$^{3/2}$), i.e., the sex pheromone of gypsy moth (Lymantria disper japonica Motschulsky) and 9.5 kg of an ethylene-vinyl acetate copolymer, followed by extruding the mixture into rods and finely cutting into pellets. Then the resulting pellets were ground using a pulverizer to give a powdery sustained release pheromone-containing preparation having an average particle size of 0.3 mm. The specific gravity thereof was found to be 0.94.

Then 8 kg of the powdery pheromone-containing preparation was mixed with 7.5 kg (solid content 50%) of an O/W type emulsion of an acrylic adhesion and 150 l of water was added to the resulting mixture. The resulting suspension was sprayed on a forest of 20 hectares using an aerial applicator. Thereafter the pheromone traps for gypsy moth were set up within the same forest in order to confirm the communication-disturbing effect of the pheromone-containing preparation. However, there was not observed any male image attracted and killed by the traps over one month.

As has been discussed above in detail, the sustained release pheromone-containing preparation according to the present invention can be sprayed using any widely used spraying machine, can release a sex pheromone at a constant concentration over a long period of time on the order of several tens of days corresponding to the copulation period of harmful insects and therefore, permits quite effective control of proliferation or breeding of harmful insects through disturbance of the copulative communication thereof. Moreover, the particles present on the preparation do not undergo any surface migration without any secondary processing.

What is claimed is:

1. A sustained-release pheromone-containing non-blocking preparation consisting essentially of a sex pheromone which is contained in powder of a synthetic resin compatible with the sex pheromone, the powder having an average particle size ranging from 0.2 to 2.5 mm wherein the sex pheromone has a heat of evaporation ranging from 21.800 to 27,000 cal/mole and a parameter, as a measure for the solubility, ranging from 8 to 9 cal$^{1/2}$cm$^{-3/2}$ and the synthetic resin, which has a parameter, as a measure for the solubility, ranging from 8 to 9.5 cal$^{1/2}$cm$^{-3/2}$ and comprises at least one member selected from the group consisting of copolymers of ethylene and vinyl esters and copolymers of ethylene and α- or β-unsaturated carboxylic acids or derivatives thereof.

2. The sustained release pheromone-containing preparation of claim 1 wherein the synthetic resin comprises at least one member selected from the group consisting of ethylene-vinyl acetate copolymers and ethylene-(meth)acrylic acid ester copolymers.

3. The sustained release pheromone-containing preparation of claim 1 wherein the sex pheromone is contained in the synthetic resin in a rate ranging from 0.3 μg to 3 mg/synthetic resin particle.

4. The sustained release pheromone-containing preparation of claim 1 wherein the sex pheromone is an aliphatic compound having a molecular weight ranging from 220 to 330.

5. The sustained release pheromone-containing preparation of claim 1 wherein the sex pheromone is at least one compound selected from the group consisting of 14-methyl-1-octadecene, Z9-tricosene, hexadecenyl acetate, hexadecadienyl acetate, hexadecatrienyl acetate, octadecenyl acetate, octadecadienyl acetate, hexadecenal, octadecenal, Z13-icosen-10-one, and 7,8-epoxy-2-methylocatadecane.

* * * * *